United States Defensive Publication [19] (H) [11] T103,403

Weiss et al. [43] Sep. 6, 1983

[54] 15-DEOXY-16-HYDROXY-16-VINYL AND CYCLOPROPYL SUBSTITUTED PROSTANOIC ACIDS AND CONGENERS

[76] Inventors: Martin J. Weiss, 975 Phyllis La., Oradell, N.J. 07649; Charles V. Grudzinskas, 21 Fifth Ave., Nyack, N.Y. 10923; Middleton B. Floyd, Jr., 5 Babbling Brook La., Suffern, N.Y. 10901; Sow-Mei L. Chen, 7 Tulip Ct., Park Ridge, N.J. 07656

[21] Appl. No.: 374,061

[22] Filed: May 3, 1982

Related U.S. Application Data

[63] Continuation of Ser. No. 201,842, Oct. 29, 1980, abandoned.

[51] Int. Cl.[3] ..... C07C 177/00

[52] U.S. Cl. ..... 560/121; 556/441; 560/231; 564/189; 564/221; 260/410.5

[57] ABSTRACT

This disclosure describes esters having prostaglandin-like activity of 15-deoxy-16-hydroxy-16-substituted-prostanoic acids formed by replacing the hydroxy group of the $C_1$-carboxylic acid substituent with para-acetamidophenoxy, methylsulfonylamido, para-acetylphenoxy, para-phenylphenoxy, $C_3$–$C_{10}$ cycloalkoxy, arylalkoxy wherein the alkoxy group has from 7–12 carbon atoms, phenoxy or phenoxy substituted with 1–3 chlorine atoms or $C_1$–$C_3$ alkyl, phenacyloxy or phenacyloxy ring-substituted with from 1–3 bromine atoms, a nitro moiety, $C_{1-C8}$ arylalkyl, or arylalkoxy wherein the alkoxy group has from 7–12 carbon atoms; substituted arylamino ($C_1$–$C_{12}$), substituted-naphthoxy, fluorenoxy, carboxyalkoxy ($C_5$–$C_{11}$), 5-indanyloxy, benzoylphenoxy, benzyloxy or ring-substituted benzyloxy, glyceryloxy, phosphatoglyceryloxy, amino substituted with an alkanoyl or cycloalkanoyl group; aroyl or substituted aroyl; alkylsulfonyl; arylsulfonyl or substituted-arylsulfonyl, hydrazinyl and substituted hydrazinyl; alkylamino ($C_1$–$C_5$), or the semicarbazide of the para-formylphenoxy group.

1 Claim, No Sheets Drawing,

105 Pages Specification

The file of this unexamined application may be inspected and copies thereof may be purchased (849 O.G. 1221, Apr. 9, 1968).